United States Patent
Chantz (10) Patent No.: US 7,671,591 B2
(45) Date of Patent: Mar. 2, 2010

(54) METHOD AND SYSTEM FOR COMPARING MICRO-ELECTRONIC DEVICES USING MAGNETIC RESONANCE IMAGING

(75) Inventor: Hyman D. Chantz, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 33 days.

(21) Appl. No.: 12/173,974

(22) Filed: Jul. 16, 2008

(65) Prior Publication Data

US 2010/0013476 A1    Jan. 21, 2010

(51) Int. Cl.
*G01V 3/00* (2006.01)

(52) U.S. Cl. .................... 324/309; 324/307
(58) Field of Classification Search .......... 324/300–322
See application file for complete search history.

(56) References Cited

U.S. PATENT DOCUMENTS

| | | | | |
|---|---|---|---|---|
| 4,543,529 | A * | 9/1985 | Mee et al. ................... | 324/313 |
| 4,689,563 | A * | 8/1987 | Bottomley et al. ........... | 324/309 |
| 5,371,464 | A * | 12/1994 | Rapoport ..................... | 324/306 |
| 5,384,536 | A | 1/1995 | Murakami et al. | |
| 5,635,840 | A * | 6/1997 | Horigane et al. ............. | 324/321 |
| 5,759,797 | A * | 6/1998 | Horigane et al. ............. | 435/29 |
| 5,886,525 | A * | 3/1999 | Yesinowski et al. .......... | 324/321 |
| 6,191,583 | B1 * | 2/2001 | Gerald et al. ................ | 324/318 |
| 6,242,915 | B1 * | 6/2001 | Hurd ............................ | 324/309 |
| 6,498,487 | B1 * | 12/2002 | Haner .......................... | 324/318 |
| 6,529,029 | B1 | 3/2003 | Bruce et al. | |
| 6,737,864 | B2 * | 5/2004 | Prammer et al. ............. | 324/303 |
| 6,911,822 | B2 * | 6/2005 | Augustine et al. ........... | 324/324 |
| 7,012,427 | B2 * | 3/2006 | Augustine et al. ........... | 324/307 |
| 7,049,505 | B2 * | 5/2006 | Kida et al. .................... | 174/36 |
| 7,064,549 | B1 * | 6/2006 | Hudson ........................ | 324/318 |
| 7,132,829 | B2 * | 11/2006 | Hudson et al. ............... | 324/318 |
| 7,164,123 | B2 * | 1/2007 | Morris et al. ................. | 250/287 |
| 7,164,267 | B2 * | 1/2007 | Prammer et al. ............. | 324/303 |
| 7,176,681 | B2 | 2/2007 | Zombo | |
| 7,205,764 | B1 * | 4/2007 | Anderson et al. ............ | 324/307 |
| 7,339,377 | B2 * | 3/2008 | Augustine et al. ........... | 324/321 |
| 7,352,179 | B2 * | 4/2008 | Chen et al. .................. | 324/303 |
| 7,417,426 | B2 * | 8/2008 | Race et al. ................... | 324/303 |
| 7,439,738 | B2 * | 10/2008 | Pines et al. .................. | 324/307 |
| 7,564,245 | B2 * | 7/2009 | Lee .............................. | 324/321 |
| 2005/0122115 | A1 | 6/2005 | Maguire et al. | |
| 2008/0068018 | A1 | 3/2008 | Massin et al. | |

* cited by examiner

*Primary Examiner*—Brij B Shrivastav
*Assistant Examiner*—Dixomara Vargas
(74) *Attorney, Agent, or Firm*—Schmeiser, Olsen & Watts; Anna Linne (57) ABSTRACT

A method of comparing micro-electronic devices. The method includes: placing a first micro-electronic device in a sample chamber of a magnetic resonance imaging machine, subjecting the first micro-electronic device to a magnetic field and a radio frequency pulse, turning off or adjusting the magnetic field and detecting a first returned RF pulse from the first micro-electronic device and storing first data relating to the first returned RF pulse; placing a second micro-electronic device in the sample chamber, subjecting the second micro-electronic device to the magnetic field and the radio frequency pulse, turning off or adjusting the magnetic field and detecting a second returned RF pulse from the second micro-electronic device and storing second data relating to the second returned RF pulse; and comparing the first data to the second data and determining if the second micro-electronic device is essentially identical to the first micro-electronic device based on the comparing.

25 Claims, 8 Drawing Sheets

RF SIGNAL IN XY SPACE KNOWN DEVICE

*FIG. 11A*

RF SIGNAL IN XY SPACE UNKNOWN DEVICE

*FIG. 11B*

RF SIGNAL IN XY SPACE DELTA

*FIG. 11C*

METHOD AND SYSTEM FOR COMPARING MICRO-ELECTRONIC DEVICES USING MAGNETIC RESONANCE IMAGING

FIELD OF THE INVENTION

The present invention relates to the field of integrated circuits; more specifically, it relates to a system and methods for comparison and validation of integrated circuits using magnetic resonance imaging.

BACKGROUND OF THE INVENTION

Integrated circuits are enormously complex structures which may contain millions of transistors and thousands of circuits. There is always a possibility that unauthorized circuits may have been inserted into integrated circuit chips during manufacture. These unauthorized circuits can, for example, cause circuit malfunctions, cause leakages of confidential data or extrusion of other information that the integrated circuit chip is processing or generating. Because of the complexity noted earlier, it is very difficult to determine if any given integrated circuit chip contains unauthorized circuits. Accordingly, there exists a need in the art to mitigate the deficiencies and limitations described hereinabove.

SUMMARY OF THE INVENTION

A first aspect of the present invention is a method, comprising: (a) placing a first micro-electronic device in a sample chamber of a magnetic resonance imaging machine, subjecting the first micro-electronic device to a static magnetic field and a radio frequency pulse, turning off or adjusting the static magnetic field and then detecting a first returned RF pulse from the first micro-electronic device and storing first data relating to the first returned RF pulse; after (a), (b) placing a second micro-electronic device in the sample chamber of the magnetic resonance imaging machine, subjecting the second micro-electronic device to the static magnetic field and the radio frequency pulse, turning off or adjusting the static magnetic field and then detecting a second returned RF pulse from the second micro-electronic device and storing second data relating to the second returned RF pulse; and (c) comparing the first data to the second data and determining if the second micro-electronic device is essentially identical to the first micro-electronic device based on the comparing.

A second aspect of the present invention is a system, comprising: a magnetic resonance imaging machine having a magnet unit, a signal processing unit and a computer, the magnet unit including a sample chamber; means for (i) subjecting micro-electronic devices placed in the sample chamber to a static magnetic field and a radio frequency pulse, (ii) turning off or adjusting the magnetic field and then (iii) detecting a returned RF pulses generated by the micro-electronic devices and (iv) storing data relating to the returned RF pulses in the computer; and means for comparing the data from a first micro-electronic device and second micro-electronic device and determining if the second micro-electronic device is essentially identical to the first micro-electronic device based on the comparing.

BRIEF DESCRIPTION OF THE DRAWINGS

The features of the invention are set forth in the appended claims. The invention itself, however, will be best understood by reference to the following detailed description of an illustrative embodiment when read in conjunction with the accompanying drawings, wherein:

DETAILED DESCRIPTION OF THE INVENTION

The term "integrated circuit" (IC) is defined as an integrated circuit chip and a package or module containing the IC. The term "integrated circuit chip" is defined as the semiconductor (e.g., silicon) die containing devices such as transistors, diodes, capacitors, resisters and inductors and the wiring layers built up on the die that interconnect the devices into circuits. The term micro-electronic device includes an IC or an integrated circuit chip.

In magnetic resonance imaging (also called nuclear magnetic resonance (NMR) imaging)) a sample is positioned in a static magnetic field and subjected to a pulsed radio frequency (RF) signal to place the sample in an excited state. The magnetic field may be turned off or adjusted and a RF return signal is produced by the sample returning to a normal from the excited state is then recorded. In order to allow spatial encoding, the static magnetic field is superimposed with a gradient magnetic field.

The term validation means the process by which an unknown micro-electronic device is "imaged" by NMR and the resulting data is compared to data from a known good or trusted micro-electronic that was NMR "imaged" and that the unknown IC micro-electronic device should be essentially identical (i.e., of identical design and within fabrication specification limits) to. Known good micro-electronic devices include those fabricated under secure conditions, those from trusted sources and those thoroughly tested and physically inspected after an NMR signature has been obtained.

Figure 1:
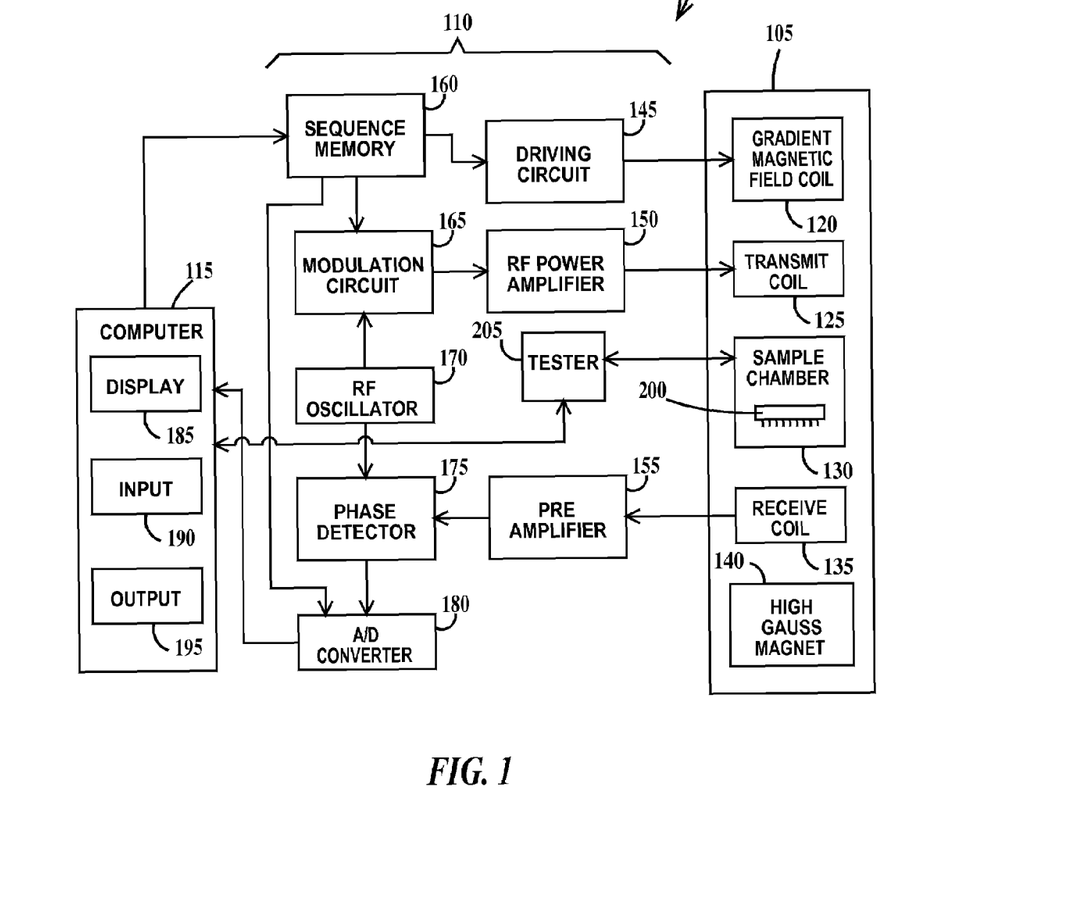
FIG. 1 a diagram of an exemplary magnetic resonance inspection system according of the present invention.

FIG. 1 is a diagram of an exemplary magnetic resonance inspection system according of the present invention. In FIG. 1, a magnetic resonance imaging (MRI) system 100 includes a magnet unit 105, a signal processing unit 110 and a computer 115. Magnet unit 105 of MRI system 100 includes a gradient magnetic field coil 120, a transmit coil 125, a sample chamber 130, a receive coil and a high gauss magnet 140 (e.g., a permanent magnet, coil magnet or super-conductive magnet). Signal processing unit 110 includes a driving circuit 145, an RF power amplifier 150, a preamplifier 155, a sequence memory 160, a modulation circuit 165, an RF oscillator 170, a phase detector 175 and an analog-to-digital (A/D) converter 180. Computer 115 includes a display 185, an input (e.g., a keyboard, mouse, disk drive) and an output (e.g., a display unit, a printer, a disk drive). Gradient magnetic field coil 120, transmit coil 125, receive coil 135 and high gauss magnet 140 are disposed so as to substantially surround sample chamber 130.

High gauss magnet 140 applies a static magnetic field having a constant strength to a sample in chamber 130. Gradient magnetic field coil 120 applies gradient magnetic fields selectively to mutually orthogonal x, y and z directions (in imaging parlance, to a slice axis, phase axis and frequency axis). Transmit coil 125 supplies a pulsed RF signal for exciting spins of atomic nuclei within a micro-electronic device 200 in sample chamber 130. Receive coil 135 detects returned RF signals from the sample in chamber 130 generated when spins of atomic nuclei within micro-electronic device 200 return to a normal state from an exited state.

Gradient magnetic field coil 120, transmit coil 125, and receive coil 135 are operatively associated with driving circuit 145, an RF power amplifier 150, and a preamplifier 155, respectively. Sequence memory 160 operates driving circuit 145 based on a stored pulse sequence in response to instructions from computer 115 to thereby apply gradient fields from gradient magnetic field coil 120 in specific directions. Sequence memory 160 also operates a modulation circuit 165 to modulate a carrier output signal from RF oscillator 170 into a pulsed RF signal of predefined timing and envelope shape. The pulsed RF signal is applied to RF power amplifier 150 and then the amplified pulsed RF signal is applied to transmit coil 125. Preamplifier 155 amplifies the return RF signal from micro-electronic device 200 in sample chamber 130 detected at receive coil 135. Preamplifier 155 amplifies the received RF signal and sends an amplified RF signal to phase detector 175. Phase detector 175 generates an analog phase-detect signal from the amplified RF signal using a carrier output signal from RF oscillator 170 as a reference signal, and supplies the phase-detected signal to A/D converter 180. A/D converter 180 converts the phase-detected analog signal into a digital signal, which is supplied to the computer 115.

Computer 115 reads and/or processes the data from A/D converter 1801, and includes algorithms in the form of computer instructions which when executed perform various signal analyses and statistical analyses on the stored data as described infra. Results of these analyses may be displayed on output unit 195. Computer 115 can also be responsible for overall control such as receiving information supplied from input 195 from an operator.

MRI system 100 includes an optional tester 205, which is connected between a socket, or probe card (not shown) in sample chamber 130 and computer 185. This allows voltage bias, analog signals, digital data patterns or combinations thereof to be applied to micro-electronic device 200 during the MRI process. Biasing, applying signals and test patterns serves two purposes. First it results in more complex return RF signals. Second, if the biasing analog signals, digital data patterns are kept secure, it is very difficult for a an unauthorized party to place a masking circuit into an unauthorized micro electronic device, the purpose of the masking circuit being is to mask the presence of the unauthorized circuit and the masking circuit in the unauthorized micro-electronic device by altering the NMR image of the unauthorized micro-electronic device to mimic that of an authorized micro-electronic device.

MRI system 100 shown in FIG. 1 is provided as an example, and it will be understood that embodiments of the invention are not limited to MRI system 100 shown in FIG. 1.

It will be understood that an MRI system 100 according to aspects of the invention can include additional components to those shown in FIG. 1 or may not include every component shown in FIG. 1.

Figure 2:
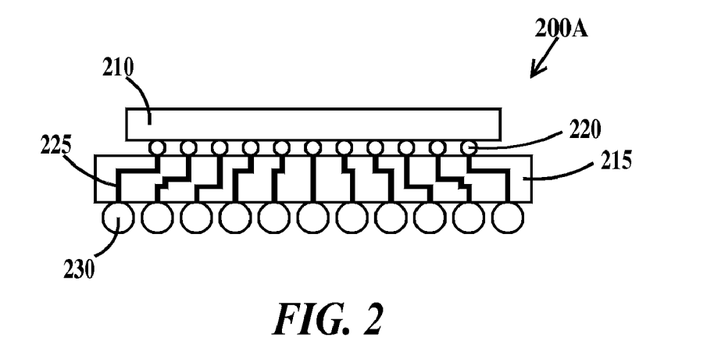
FIG. 2 is a cross-section through an exemplary first type of integrated circuit.

FIG. 2 is a cross-section through an exemplary first type of integrated circuit. In FIG. 2, an IC 200A includes an integrated circuit chip 210 physically and electrically connected to a module 215 by solder bumps 220. Wires 225 in module 225 connect solder bumps 220 to solder balls 230. Module 215 may be organic (e.g., fiberglass) or ceramic and wires 25 may comprise one or more wiring layers. Solder balls 230 are designed for surface mounting IC 200A directly to a printed circuit board (PCB). Solder balls 230 may be replaced by solder columns. Solder balls 230 may be replaced with pins, which can be used to mount ICs into sockets, which are mounted on a PCB or mounted directly to a PCB. IC 200A is thus an example of an IC that uses flip-chip (or C4) technology.

Figure 3:
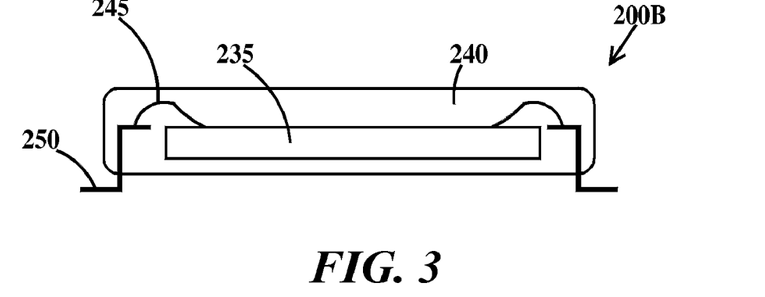
FIG. 3 is a cross-section through an exemplary second type of integrated circuit.

FIG. 3 is a cross-section through an exemplary second type of integrated circuit. In FIG. 3, an IC 200B includes and integrated circuit chip contained within a plastic package 240. Wire bonds 245 electrically connect integrated circuit chip 235 to leads 250. Leads 250 are designed for surface mounting IC 200B directly to a PCB. Leads 250 may be replaced with pins, which can be used to mount ICs into sockets, which are mounted on a PCB or mounted directly to a PCB. The leads on some plastic packages are designed to be mounted in sockets on a PCB. IC 200B is thus an example of plastic packaging technology.

Figure 4:
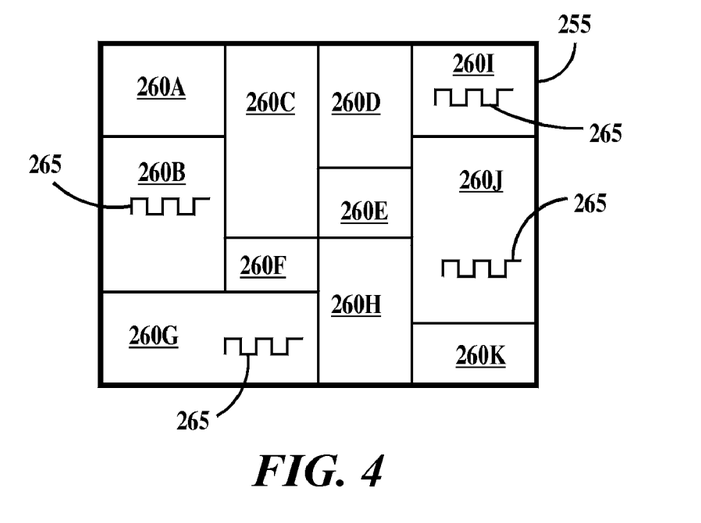
FIG. 4 is a top view of an exemplary integrated circuit chip for enhanced device comparison according embodiments of the present invention.

FIG. 4 is a top view of an exemplary integrated circuit chip for enhanced comparison according embodiments of the present invention. In FIG. 4, an exemplary integrated circuit chip 255 includes regions 260A, 260B, 260C, 260D, 260E, 260F, 260G, 260H, 260I, 269J and 260K. There may be more or less regions than illustrated in FIG. 4. These regions often correspond to cores, which are pre-designed circuit functions. For example, a microprocessor may contain multiple processing cores, memory cores, arithmetic cores etc. Formed, by way of example, in cores 260B, 260G, 260I and 260J are serpentine signal enhancing structures 265 which are not electrically connected to any wire or device (e.g., transistor, diode, resistor, capacitor or inductor) of integrated circuit chip 255. Signal enhancing structures 265 may comprise an electrical conductor, a magnetic material, or an electrically conductive magnetic material. Signal enhancing structures 265 are designed to interact with the magnetic fields from gradient magnetic field coil 120 and high gauss magnet 140 of MRI system 100 (see FIG. 1) to generate a more complex return RF signal.

Figure 5:
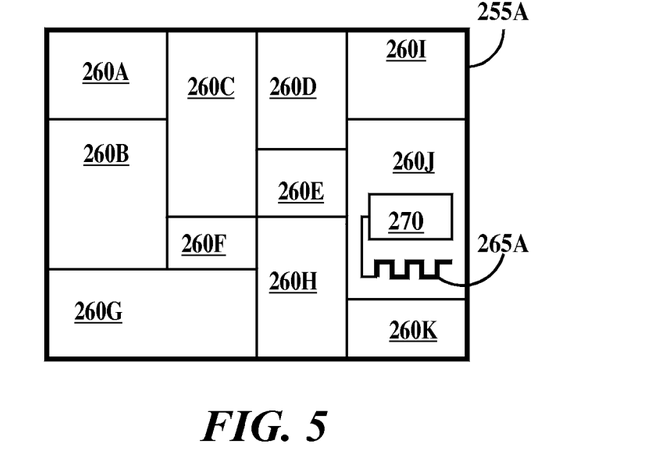
FIG. 5 is a top view of an exemplary integrated circuit chip for preventing unauthorized comparison according embodiments of the present invention.

FIG. 5 is a top view of an exemplary integrated circuit chip for preventing or detecting comparison according embodiments of the present invention. In FIG. 5, an integrated circuit chip 255A (similar to integrated circuit chip 255 of FIG. 4) includes a serpentine structure 265A connected to a destruct circuit 270. Serpentine structure 265A acts as an inductor which generates a current when subjected to a varying magnetic field. The current may be used by destruct circuit 270 to program fuses or activate transistors to render integrated circuit 155A inoperable or to leave a signature that can later be read to indicate if an attempt at NMR imaging" has been performed on integrated circuit chip 255A. In one example, serpentine structure 265A is designed to not be detectable by X-ray imaging.

Figure 6A:
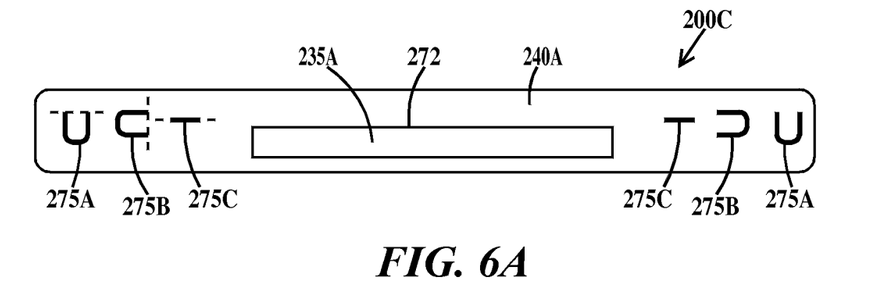
FIG. 6A is a cross-sectional view of an integrated circuit containing devices to flag an unauthorized comparison attempt according embodiments of the present invention.

FIG. 6A is a cross-sectional view of an integrated circuit containing devices to flag an unauthorized comparison attempt according embodiments of the present invention. In FIG. 6A, an IC 200C includes an integrated circuit chip 235A in a plastic package body 240A. A set (two sets are shown in the example of FIG. 6A) of three "horseshoe" magnets 275A, 275B and 275C are placed in body 240A. They are aligned so respective lines (dashed lines) passing through the poles of each magnet are mutually orthogonal. In FIG. 6A, the line passing through the poles of magnets 275A and 275C are in planes parallel to the top surface 272 of integrated circuit chip 235A. Other pole orientations are possible. In one example, only a single horseshoe magnet is used. Horseshoe shaped magnets may be replaced by other shaped magnets such as bar magnets and disc magnets.

Figure 6B:
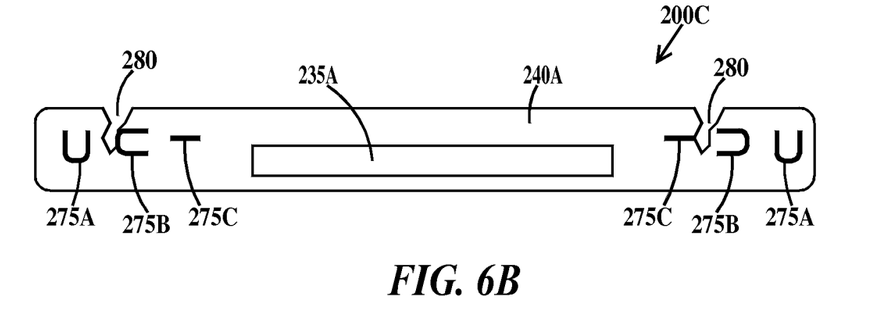
FIG. 6B is a cross-sectional view of the integrated circuit of FIG. 6A after an unauthorized comparison attempt according embodiments of the present invention.

FIG. 6B is a cross-sectional view of the integrated circuit of FIG. 6A after an unauthorized comparison attempt according embodiments of the present invention. When magnets 275A, 275B and 275C are subjected to the intense magnetic field generated in an NMR machine, magnets 275A, 275B and 275C are pulled/pushed by that field so strongly that cracks 280 are formed in body 240A.

Figure 7:
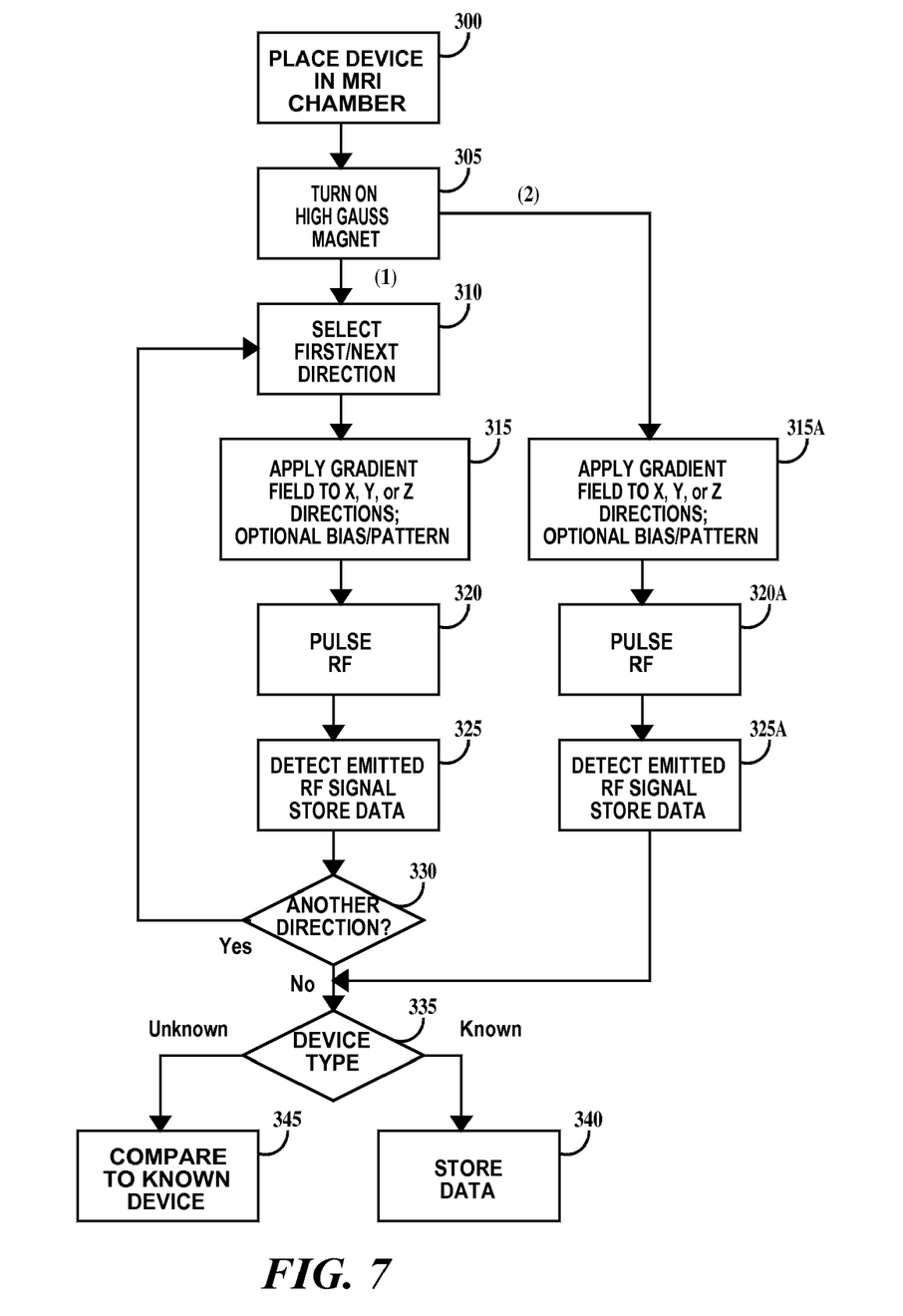
FIG. 7 is a flowchart of methods of comparison according to embodiments of the present invention.

FIG. 7 is a flowchart of methods of comparison according to embodiments of the present invention. The steps of the flowchart of FIG. 7 are performed first on a known or trusted micro-electronic device and then on an unknown (or suspect) micro-electronic device that and essentially identical to the known micro-electronic device (i.e., identically designed and within fabrication specification limits). For the integrated circuit chip specification limits define allowable variations in material and structure and include, for example, the allowable differences in metal line widths and thickness differences in metal and insulating layers. For the package of the IC specification limits define allowable variations in material and structure and include, for example, package dimensions, size of solder bumps, positions and size of wire bonds, widths and thickness of land in modules.

In step 300 an IC (or integrated circuit is placed in the MRI chamber. In step 305 the high gauss magnetic field is turned on. In one example, the high gauss magnetic field has a field strength of between about a 0.5 tesla and about 10 tesla and is applied in the z direction. The method can know follow one of two mutually exclusive paths. The first is the path (1) through steps 310, 315, 320, 325 and 330 to step 335. The second path (2) is through steps 315A, 320A and 325A to step 335. The unknown micro-electronic device advantageously follows the same path and is subjected to the same NMR conditions as the known micro-electronic device.

In step 310, a direction (x, y or z) is selected. In step 315, a gradient magnetic field of, for example, 1 tesla is applied in the selected direction and in step 320 a RF pulse is directed to the IC. In step 325 the emitted (returned) RF signal is detected and information describing the return RF signal (which is also a pulse) is stored. The duration and time of reception of the return RF signal will vary. In step 330, if another direction of the three possible directions (x, y, z) is selected and the method loops back to step 310. This loop will repeat three times, once for each direction.

In path (2) in step 315A, gradient magnetic fields are applied in the x, y, and z directions simultaneously. Each gradient field may have a same or a different field strength of between about 0.5 tesla and about 10 tesla. Steps 320A and 325A are similar to steps 320 and 325 respectively.

In steps 315 and 315A, optional test conditions (i.e., voltage bias, analog signal, digital data pattern or combinations thereof) may be applied to the micro-electronic device. In a first example, optional test conditions are applied only during step 315 (or 315A). In a second example, optional test conditions are applied the only during steps 315 and 320 (or 315A and 320A). In a third example, the optional test conditions are applied the only during steps 305, 310, 315 and 320 (or 305, 315A and 320A). In a fourth example, the optional test conditions are applied during steps 305, 310, 315, 320 and 325 (or 305, 315A, 320A and 325A).

In step 335, the IC is removed from the MRI chamber and it is determined whether the micro-electronic device was a known micro-electronic device or an unknown micro-electronic device. If the micro-electronic device was a known micro-electronic device then in step 340 analyses are performed and the analyses data is stored. If the micro-electronic device was an unknown micro-electronic device then in step 345 analyses are performed and the analyses is compared to analyses previously stored from a known micro-electronic device MRI "images" under the same MRI (and bias/pattern) conditions. If the compare is within predefined limits the unknown micro-electronic device is validated. It does not matter whether the known or unknown micro-electronic device is run first, but the comparison cannot be performed until both known or unknown micro-electronic devices have been run and the respective data analyzed.

Figure 8A:
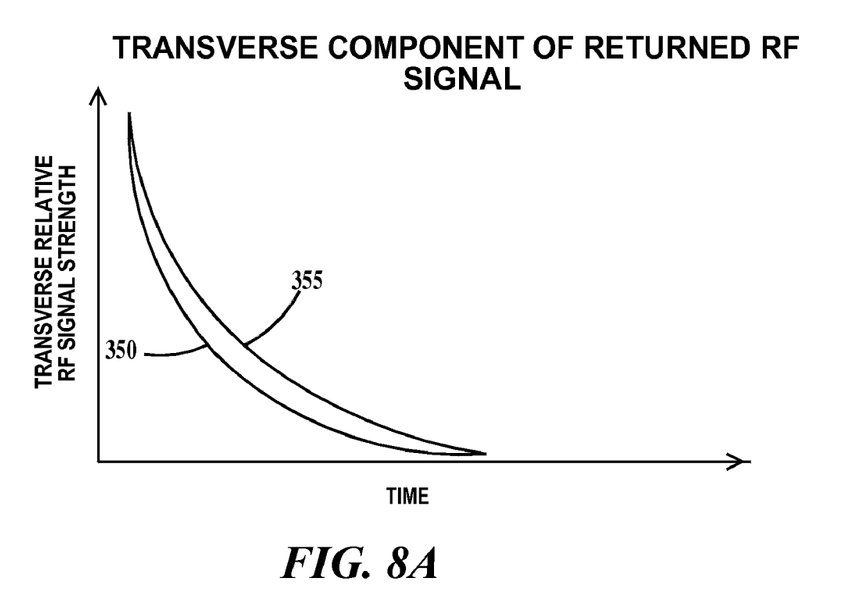
FIGS. 8A and 8B illustrate a first method of data analysis for comparison according to embodiments of the present invention.
Figure 8B:
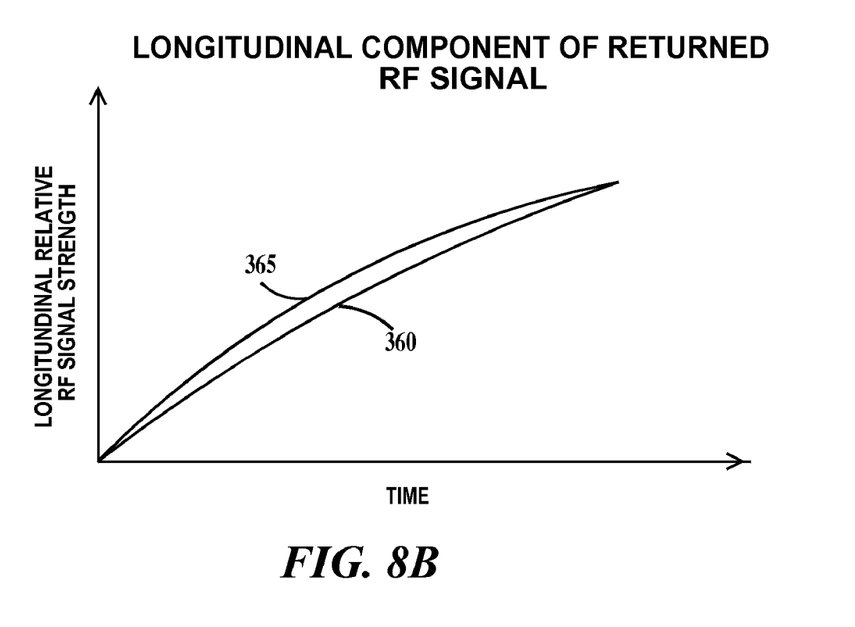

FIGS. 8A and 8B illustrate a first method of data analysis for comparison according to embodiments of the present invention. FIG. 8A is a plot of the transverse component of the returned RF signal for a known micro-electronic device 350 and an unknown micro-electronic device 355 as relative RF strength versus time. Direct comparison or statistical analysis of the difference between curves 350 and 355 is performed to determine if the unknown micro-electronic device is significantly different from the unknown micro-electronic device. In FIG. 8A, the difference between curve 355 relative to curve 350 is shown as a positive time shift. The shift may be negative. FIG. 8B is a plot of the longitudinal component of the returned RF signal for a known micro-electronic device 360 and an unknown micro-electronic device 365 as relative RF strength versus time. Direct comparison or statistical analysis of the difference between curves 360 and 365 is performed to determine if the unknown micro-electronic device is significantly different from the unknown micro-electronic device. In FIG. 8B, the difference of curve 365 relative to curve 360 is shown as a negative time shift. The shift may be positive.

Figure 9A:
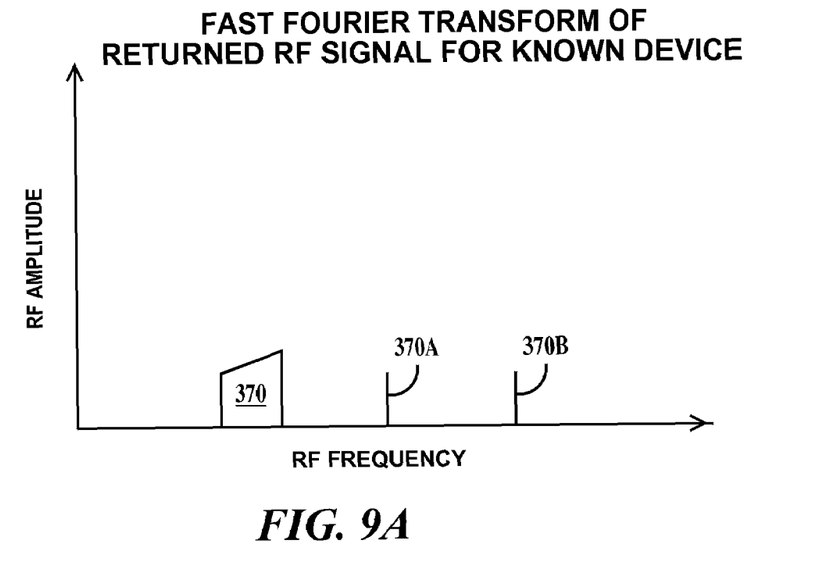
FIGS. 9A and 9B illustrate a second method of data analysis for comparison according to embodiments of the present invention.
Figure 9B:
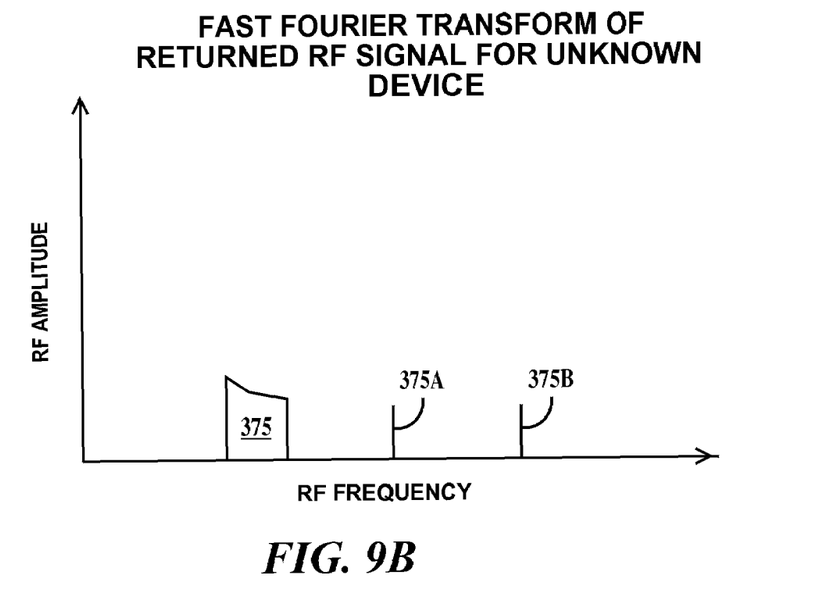

FIGS. 9A and 9B illustrate a second method of data analysis for comparison according to embodiments of the present invention. FIG. 9A is a plot of a fast Fourier transform of the returned RF signal for a known IC (or integrated circuit) as RF amplitude versus RF frequency. Element 370 is the returned signal and elements 370A and 370B are harmonic artifacts of element 370. FIG. 9B is a plot of a fast Fourier transform of the returned RF signal for an unknown IC (or integrated circuit) as RF amplitude versus RF frequency. Element 375 is the returned signal and elements 375A and 3750B are harmonic artifacts of element 370. Element 370 and 375 are statistically compared in terms of amplitude of a given frequency range to determine if the unknown micro-electronic device is significantly different from the unknown micro-electronic device. In FIGS. 9A and 9B, the amplitude of the returned RF signal has been transferred from a time domain to a frequency domain.

Figure 10A:
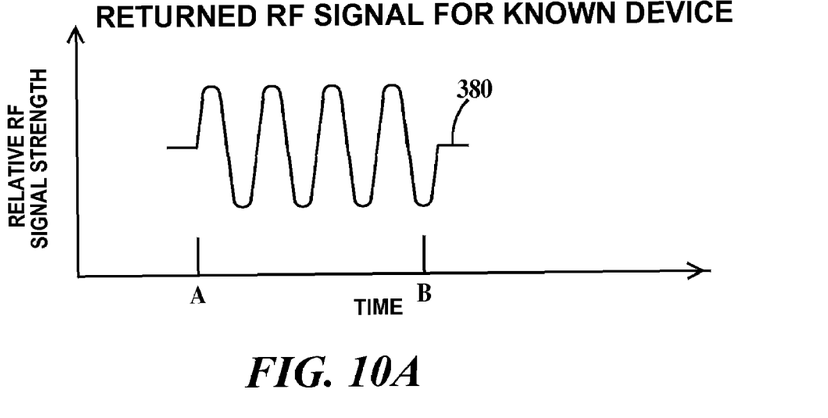
FIGS. 10A, 10B and 10C illustrate a third method of data analysis for comparison according to embodiments of the present invention.
Figure 10B:
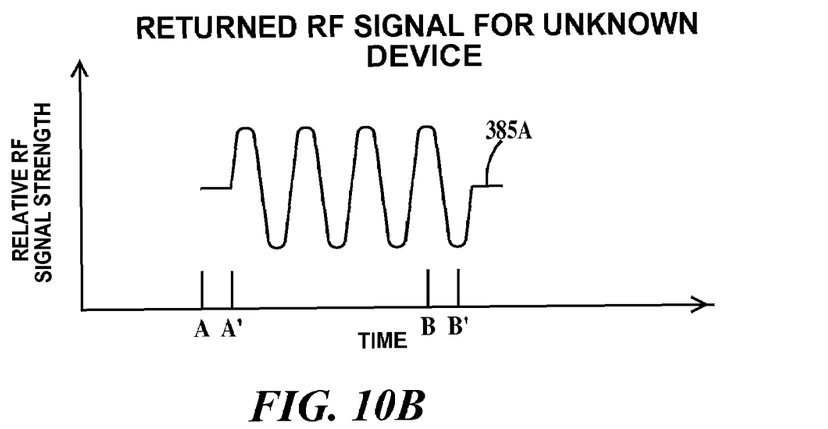
Figure 10C:
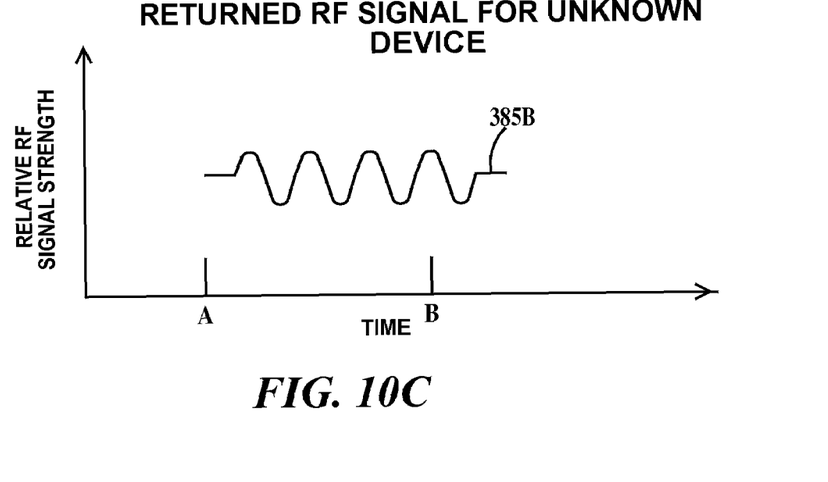

FIGS. 10A, 10B and 10C illustrate a third method of data analysis for comparison according to embodiments of the present invention. FIG. 10A is a plot of the returned RF signal as relative RF signal strength versus time for a known micro-electronic device. RF signal 380 has a fixed amplitude between times A and B measured from when the RF pulse signal terminated (or other convenient time reference). An unknown micro-electronic device may exhibit a signal that is offset ion amplitude, phase, frequency or combinations thereof. Two simple examples are given in FIGS. 10B and 10C.

FIG. 10B is a plot of the returned RF signal as relative RF signal strength versus time for an unknown micro-electronic device having only a frequency shift. RF signal 385A has fixed amplitude between times A' and B' measured from the same reference as A and B of FIG. 10A. The shift between A and A' and B and B' is statistically to determine if the unknown micro-electronic device is significantly different from the unknown micro-electronic device.

FIG. 10C is a plot of the returned RF signal as relative RF signal strength versus time for an unknown micro-electronic device having only an amplitude shift. RF signal 385B has a fixed amplitude between times A and B measured from the same reference as A and B of FIG. 10A. The change in amplitude between curve 380 of FIG. 10A and curve 385B of FIG. 10C is statistically to determine if the unknown micro-electronic device is significantly different from the unknown micro-electronic device.

It will be appreciated that a complete statistical analysis would compare time, amplitude, frequency and phase differences of the curves described in FIGS. 10A, 10B and 10C.

Figure 11A:
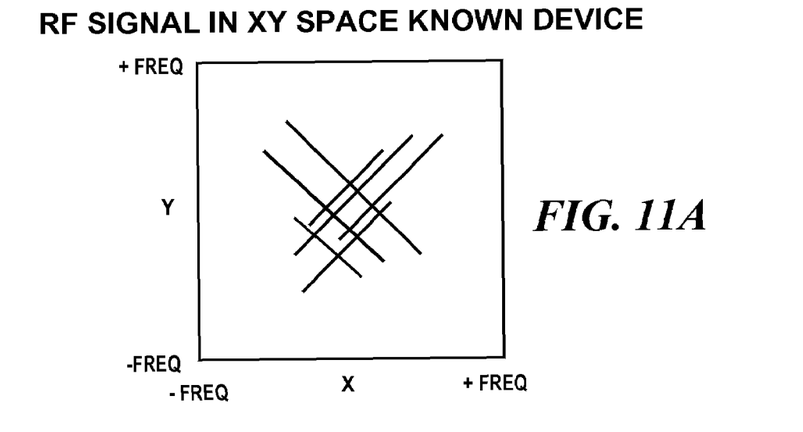
FIGS. 11A, 11B and 11C illustrate a fourth method of data analysis for comparison according to embodiments of the present invention.
Figure 11B:
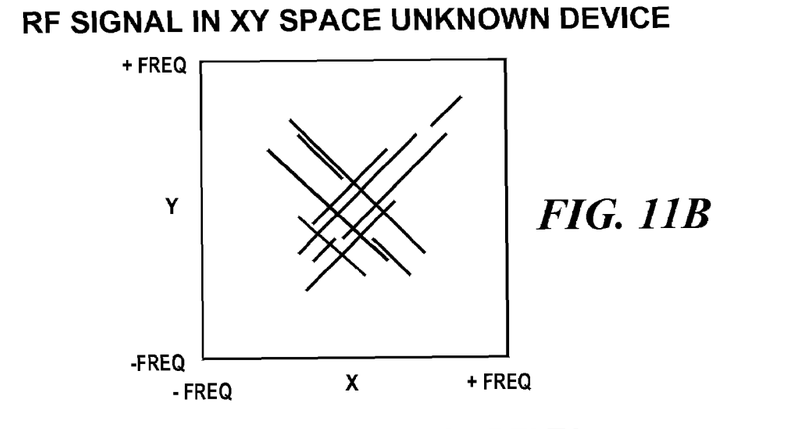
Figure 11C:
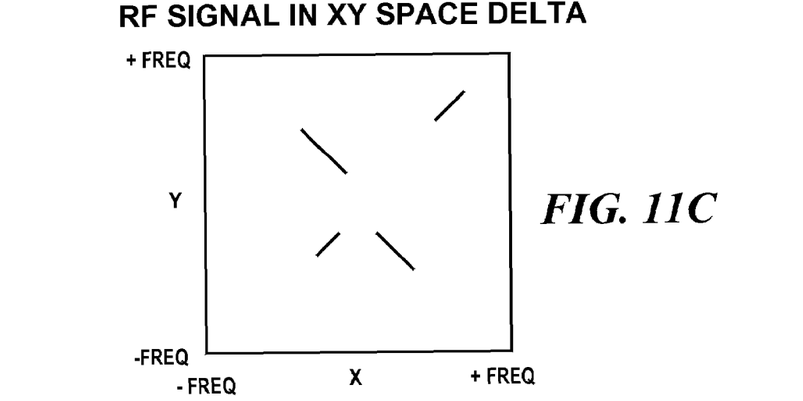

FIGS. 11A, 11B and 11C illustrate a fourth method of data analysis for comparison according to embodiments of the present invention. FIG. 11A is a plot of the returned RF signal XY space (at a selected Z) as a function of frequency for a known micro-electronic device. As such FIG. 11A is closer to what is may be considered an "image." FIG. 11B is a plot of the returned RF signal XY space (at the selected Z) as a function of frequency for an unknown micro-electronic device. FIG. 11C is a plot of the delta between the plot of FIG. 11A and that of FIG. 11B. The amount of structure (and optionally the position of the structures) is statistically analyzed to determine if the unknown micro-electronic device is significantly different from the unknown micro-electronic device. FIG. 11C is FIG. 11A "subtracted" from FIG. 11A.

Thus the embodiments of the present invention allow for relatively quick and inexpensive validation of integrated circuit chips.

The description of the embodiments of the present invention is given above for the understanding of the present invention. It will be understood that the invention is not limited to the particular embodiments described herein, but is capable of various modifications, rearrangements and substitutions as will now become apparent to those skilled in the art without departing from the scope of the invention. Therefore, it is intended that the following claims cover all such modifications and changes as fall within the true spirit and scope of the invention.

What is claimed is:

1. A method, comprising:
   (a) placing a first micro-electronic device in a sample chamber of a magnetic resonance imaging machine, subjecting said first micro-electronic device to a static magnetic field and a radio frequency pulse, turning off or adjusting said static magnetic field and then detecting a first returned RF pulse from said first micro-electronic device and storing first data relating to said first returned RF pulse;
   after (a), (b) placing a second micro-electronic device in said sample chamber of said magnetic resonance imaging machine, subjecting said second micro-electronic device to said static magnetic field and said radio frequency pulse, turning off or adjusting said static magnetic field and then detecting a second returned RF pulse from said second micro-electronic device and storing second data relating to said second returned RF pulse; and
   (c) comparing said first data to said second data and determining if said second micro-electronic device is essentially identical to said first micro-electronic device based on said comparing.

2. The method of claim 1, wherein:
   (a) includes superimposing a gradient magnetic field on said static magnetic field and turning off said gradient magnetic field before said detecting said first returned RF signal; and
   (b) includes superimposing said gradient magnetic field on said static magnetic field and turning off said gradient magnetic field before said detecting said second returned RF signal.

3. The method of claim 2, wherein said gradient magnetic fields consists of first, second and third gradient magnetic fields applied in respective mutually orthogonal directions.

4. The method of claim 1, wherein:
   The method of claim 1, wherein:
   (a) includes:
      superimposing a first gradient magnetic field on said static magnetic field and turning off said first gradient magnetic field before said detecting said first returned RF signal;
      superimposing a second gradient magnetic field on said static magnetic field and turning off said second gradient magnetic field before detecting a third returned RF signal and storing third data relating to said third returned RF signal; and
      superimposing a third gradient magnetic field on said static magnetic field and turning off said third gradient magnetic field before detecting a fifth returned RF signal and storing fifth data relating to said fifth returned RF signal;
   (b) includes:
      superimposing said first gradient magnetic field on said static magnetic field and turning off said first gradient magnetic field before said detecting said second returned RF signal;
      superimposing said second gradient magnetic field on said static magnetic field and turning off said second gradient magnetic field before detecting a fourth returned RF signal and storing fourth data relating to said fourth returned RF signal; and
      superimposing said third gradient magnetic field on said static magnetic field and turning off said third gradient magnetic field before detecting a sixth returned RF signal and storing sixth data relating to said sixth returned RF signal; and
   (c) further includes comparing said third data to said fourth data and comparing said fifth data to said sixth data in said determining if said second micro-electronic device is essentially identical to said first micro-electronic device based on said comparing.

5. The method of claim 4, wherein said first, second and third gradient magnetic fields are applied in respective mutually orthogonal directions.

6. The method of claim 1, wherein said comparing includes comparing data representing a transverse component of said first returned RF signal to data representing a transverse component of said second returned RF signal.

7. The method of claim 1, wherein said comparing includes comparing data representing a longitudinal component of said first returned RF signal to data representing a longitudinal component of said second returned RF signal.

8. The method of claim 1, wherein said comparing includes comparing a fast Fourier transform from a time domain to frequency domain of data representing said first returned RF signal to a fast Fourier transform from a time domain to frequency domain of data representing said second returned RF signal.

9. The method of claim 1, wherein said comparing includes comparing data representing a frequency, phase and amplitude of said first returned RF signal to data representing a frequency, phase and amplitude of said second returned RF signal.

10. The method of claim 1, wherein said comparing includes comparing data representing a two dimensional image of said first micro-electronic device to data representing a two dimensional image of said second micro-electronic device.

11. The method of claim 1, further including:
during (a) applying voltage bias, analog signals, digital data patterns or combinations thereof to said first micro-electronic device; and
during (a) applying said voltage bias, said analog signal, said digital data pattern or said combinations thereof to said second micro-electronic device.

12. The method of claim 1, wherein said micro-electronic device is an integrated circuit chip.

13. The method of claim 1, wherein said micro-electronic device is an integrated circuit chip in a package.

14. The method of claim 1, wherein said first micro-electronic device includes a first serpentine signal enhancing structure, said first serpentine signal enhancing structure not electrically connected to any wire or device of said first micro-electronic device and said second micro-electronic device includes a second serpentine signal enhancing structure, said second serpentine signal enhancing structure not electrically connected to any wire or device of said second micro-electronic device, said first serpentine signal enhancing structure and said second serpentine signal enhancing structure identically designed.

15. A system, comprising:
a magnetic resonance imaging machine having a magnet unit, a signal processing unit and a computer, the magnet unit including a sample chamber;
means for (i) subjecting micro-electronic devices placed in said sample chamber to a static magnetic field and a radio frequency pulse, (ii) turning off or adjusting said magnetic field and then (iii) detecting a returned RF pulses generated by said micro-electronic devices and (iv) storing data relating to said returned RF pulses in said computer; and
means for comparing said data from a first micro-electronic device and second micro-electronic device and determining if said second micro-electronic device is essentially identical to said first micro-electronic device based on said comparing.

16. The system of claim 15, wherein said means for comparing includes algorithms in the form of computer instructions that when executed perform signal analyses and statistical analysis on said data relating to said returned RF pulses.

17. The system of claim 16, wherein an algorithm of said algorithms compares data representing transverse components of said returned RF signals from two micro-electronic devices.

18. The system of claim 16, wherein an algorithm of said algorithms compares data representing longitudinal components of said returned RF signals from two micro-electronic devices.

19. The system of claim 16, wherein an algorithm of said algorithms compares fast Fourier transforms from time domains to frequency domains of data representing said returned RF signals from two micro-electronic devices.

20. The system of claim 16, wherein an algorithm of said algorithms compares data representing frequencies, phase and amplitudes of said returned RF signal from two micro-electronic devices.

21. The system of claim 16, wherein an algorithm of said algorithms compares data representing two dimensional images of two micro-electronic devices.

22. The system of claim 15, further including:
means for applying voltage bias, analog signal, digital data pattern or combinations thereof to said micro-electronic devices.

23. The system of claim 15, wherein said micro-electronic device is an integrated circuit chip.

24. The system of claim 15, wherein said micro-electronic device is an integrated circuit chip in a package.

25. The system of claim 15, further including:
means for superimposing a gradient magnetic field on said static magnetic field and turning off said gradient magnetic field before said detecting said returned RF signals.

* * * * *